United States Patent [19]

Acton et al.

[11] 4,086,416
[45] Apr. 25, 1978

[54] SEPTACIDIN ANALOGS

[75] Inventors: Edward M. Acton, Menlo Park; Kenneth J. Ryan, Sunnyvale, both of Calif.

[73] Assignee: Stanford Research Institute, Menlo Park, Calif.

[21] Appl. No.: 797,591

[22] Filed: May 17, 1977

[51] Int. Cl.² ............................................. C07H 19/16
[52] U.S. Cl. ...................................... 536/24; 424/180
[58] Field of Search ..................................... 536/24, 53

[56] References Cited
U.S. PATENT DOCUMENTS 3,155,647  11/1964  Dutcher et al. .................... 536/24

Primary Examiner—Johnnie R. Brown
Assistant Examiner—Blondel Hazel
Attorney, Agent, or Firm—Donovan J. De Witt

[57] ABSTRACT

Septacidin analogs, useful as antitumor agents, having the structure

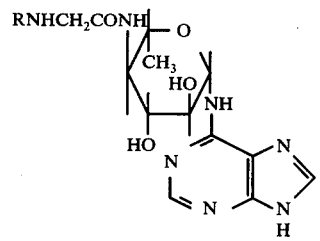

where R is a branched or straight chain alkanoyl group of from 12 to 16 carbon atoms. A preferred compound is 6-[4,6-dideoxy-4-(isopalmitoylglycyl)-amino-β-L-glucopyranosylamino]-9H-purine.

3 Claims, No Drawings

SEPTACIDIN ANALOGS

The invention described herein was made in the course of work under a grant or award from the Department of Health, Education, and Welfare.

BACKGROUND OF INVENTION — PRIOR ART

As more particularly recited below, the present invention relates to antitumor septacidin analogs. The closest prior art of which applicants are aware is U.S. Pat. No. 3,155,647 issued Nov. 3, 1964 to Dutcher et al. which discloses septacidin and other of its analogs. However, those compounds so disclosed which are otherwise similar to those of the present invention differ therefrom in that they have a mono- or polyhydroxyalkyl group attached at C.5 to the ring comprising the sugar moiety rather than the methyl group which characterizes the compounds of the present invention. While the compounds of the Dutcher et al. patent are disclosed as having physiological activity and utility as fungicides, the literature discloses that said compounds also have antitumor characteristics.

While the compounds of the Dutcher et al. patent were produced by fermentation, those of the present invention were prepared by a synthetic route. The general approach employed was to start with the sugar, construct on to it the adenine moiety, and attach the fatty acid-amino acid chain last.

SUMMARY OF THE INVENTION

The present invention relates to novel septacidin analogs having the structure

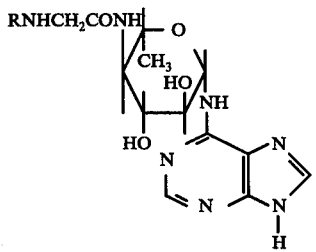

where R is a branched or straight chain alkanoyl group of from 12 to 16 carbon atoms. A preferred compound by reason of its enhanced antitumor activity is 6-[4,6-dideoxy-4-(isopalmitoylglycyl)amino-β-L-glucopyranosylamino]-9H-purine. Antitumor data in animals are available for this compound as well as for 6-[4,6-dideoxy-4-(lauroylglycyl)amino-β-L-glucopyranosylamino]-9H-purine. The preparation of the first of these compounds is set forth in Example 1 below. The other of the aforesaid compounds form the subject of Example 2. Data presently available as to the antitumor activity (in mice) of these compounds is set forth in the table following the examples.

Others of the compounds which come within the scope of the structural formula given above include those wherein the isopalmitoyl and lauroyl groups of the present compounds (where R has a value of 16 and 12, respectively) are replaced by palmitoyl, myristoyl, tridecanoyl, pentadecanoyl groups or other like alkanoyl groups of from 12 to 16 carbon atoms. It is believed that these compounds will also manifest useful antitumor qualities and it is anticipated that the said activity of these compounds, as well as that of the compounds of Examples 1 and 2, will carry over into man.

EXAMPLE I

6-[4,6-Dideoxy-4-(isopalmitoylglycyl)amino-β-L-glucopyranosylamino]-9H-purine

The following paragraphs A - H describe the preparation of various intermediates leading to the sugar adenine moiety which is designated as 6-(4-amino-4,6-dideoxy-β-L-glucopyranosylamino)-9H-purine:

A. 2,3-Di-O-benzoyl-6-deoxy-4-O-methanesulfonyl-α-L-galactopyranosyl chloride. A solution of 60.0 g (0.129 mol) of methyl 2,3-di-O-benzoyl-6-deoxy-4-O-methanesulfonyl-α-L-galactopyranoside (A. C. Richardson and J. M. Williams, Tetrahedron, 23, 1641 (1967)), mp 161°–163°, in 1.5 l of anhydrous benzene at room temperature was treated with 10 ml of titanium tetrachloride and then a slow stream of anhydrous HCl gas for 30 min. The orange-yellow solution was stored at room temperature for 18 hr protected from moisture. It was washed with two 700-ml portions of ice water, 700 ml of saturated NaHCO$_3$ solution, and another 700 ml of water. The benzene solution was dried and evaporated to a syrup (ca. 150 ml), which was dissolved in 100 ml of ClCH$_2$CH$_2$Cl. Petroleum ether (b.p. 60°–110°) was added to the cloud point (ca. 250 ml required), and the mixture was seeded and chilled at 3° (seed crystals were obtained by scratching the syrup on a watch glass with ClCH$_2$CH$_2$Cl-pet. ether). After 18 hr, an additional 100 ml of petroleum ether was added, and chilling was continued for 3 da. The white solid was collected by filtration to yield 50.6 g (84%), m.p. 124.5°–126°.

B. 2,3-Di-O-benzoyl-6-deoxy-4-O-methanesulfonyl-β-L-galactopyranosyl azide. The chlorosugar of paragraph A (54.6 g, 0.116 mol) was added to 500 ml of Me$_2$SO, followed by 55 g (0.85 mol) of NaN$_3$, and the mixture was stirred at room temperature for 18 hr. The chlorosugar dissolved rapidly, and NaCl slowly precipitated. The mixture was poured into 3.2 l of water, and stirring was continued for 1 hr. The white solid precipitate was collected on a filter, and while still wet was dissolved in 2.8 l of boiling MeOH. The solution was cooled in ice for 1 hr, and the white precipitate was collected to yield 42 g (76%), mp 152.5°–154°.

C. 4-Amino-6-(2,3-di-O-benzoyl-6-deoxy-4-O-methanesulfonyl-β-L-galactopyranosylamino)-5-nitropyrimidine. A solution of 10.5 g (0.022 mol) of the 1-azide of paragraph B in 100 ml of anhydrous benzene was treated with 1.1 g of Pd black and shaken under H$_2$ at 2–3 atm for 7 days. The catalyst was removed by filtration, washed with 20 ml of benzene, and the combined filtrate containing the resultant amine was used immediately without exposure to moisture. 4-Amino-6-chloro-5-nitropyrimidine (4.0 g, 0.023 mol) was dissolved in 100 ml of refluxing anhydrous benzene, 10 ml of benzene was removed by azeotropic distillation to ensure dryness, and the hot solution (sometimes containing a little precipitate) was treated with the above solution of amine followed by 2.3 g (0.023 mol) of Et$_3$N. Another 10 ml of benzene was distilled off and the mixture protected from moisture was refluxed for 18 hr. The mixture was cooled, treated with 1 ml of Et$_3$N and 1 ml of H$_2$O, stirred overnight, and filtered. The filtrate was evaporated to dryness. The residue was dissolved in 300 ml of boiling 95% EtOH. The solution was allowed to cool very slowly to room temperature, while much of the product separated as crystals. The mixture was kept at room temperature for 2 days and filtered to yield 9.1 g (70%) that was used in the next step, mp 158°–165°.

D. 4,5-Diamino-6-(2,3-di-O-benzoyl-6-deoxy-4-O-methanesulfonyl-β-L-galactopyranosylamino)-pyrimidine. A solution of 10.1 g (0.017 mol) of nitro compound of paragraph C in 200 ml of anhydrous pyridine was treated with 20 ml of a pyridine slurry of Raney Active Nickel Catalyst (Grace) (prewashed with pyridine to remove water). The mixture was shaken under 2–3 atm of $H_2$ for 2 hr and filtered. The collected nickel was washed with 200 ml of pyridine, and the combined filtrates were evaporated to dryness. The residue was dissolved in 250 ml of $CHCl_3$. The solution was washed with 250 ml of saturated aqueous NaCl, dried, and evaporated to dryness. The solid residue was triturated with 150 ml of boiling benzene and filtered while hot. The insoluble portion was washed with 25 ml of hot benzene. The combined filtrate was chilled at 3°–5° for 3 days to yield 7.0 g (73%) of an amorphous brown precipitate, mp 195°–197°, that was homogeneous by TLC on alumina, $R_f$ 0.78 in $CHCl_3$-MeOH (19:1); $[\alpha]_D^{21}$ −51.4° (c 1, $Me_2SO$).

E. 6-(2,3-Di-O-benzoyl-4-O-methanesulfonyl-6-deoxy-β-L-galactopyranosylamino)-9H-purine. A mixture of 138 g (0.247 mol) of the diamine of paragraph D, 250 ml of triethyl orthoformate, and 250 ml of acetic anhydride was heated to reflux (slight exotherm). The resultant solution was stirred and refluxed for 2 hr, cooled, and evaporated in vacuo. The oily residue was dissolved in 2.5 l of hot benzene, and the solution was diluted to the cloud point with cyclohexane (ca. 300 ml), clarified by heating, allowed to cool slowly to room temperature, and stored for 24 hr. The precipitate was collected by filtration to yield 105 g of dark brown solid, mp 155°–167°. The filtrate was concentrated to 500 ml, diluted to the cloud point with more cyclohexane, chilled at 5° for 8 days, and filtered to yield 35 g of a second crop, mp 152°–165° (total yield 140 g, 99%). The product, $R_f$ 0.47 in $CHCl_3$-MeOH (19:1), was acceptable for use in the next step. Reprecipitation by cooling a benzene solution afforded a chromatographically homogeneous sample for analysis (25% yield), mp 156°–178°.

F. 6-(4-Azido-2,3-di-O-benzoyl-4,6-dideoxy-β-L-glucopyranosylamino)-9H-purine. A mixture of 14.0 g (24.4 mmol) of the compound of paragraph E and 7.2 g (110 mmol) of $NaN_3$ in 72 ml of $Me_2SO$ was stirred and heated at 100° for 18 hr, and poured into 1 l of ice and water. After 30 min of stirring, the precipitate was collected and dissolved in 200 ml of $CHCl_3$. The solution was washed into 100 ml of saturated brine, dried, and evaporated to yield 13.8 g (109%) of a residual foamed-glass product; TLC, $R_f$ 0.50 on silica gel in $CHCl_3$-MeOH (19:1).

G. 6-(4-Azido-4,6-dideoxy-β-L-glucopyranosylamino)-9H-purine. A solution of 175 g (0.340 mol) of the product of paragraph F and 27 g (0.50 mol) of NaOMe (Aldrich; anhydrous powder) in 1.2 l of anhydrous MeOH was protected from moisture and stirred at room temperature for 2 hr, then treated with ca. 500 g of 100- to 200-mesh Dowex 50 (H) ion exchange resin to neutralize the base and absorb the purine. After one more hour of stirring, the resin was collected, washed with 200 ml of MeOH (to remove MeOBz), added to a chromatographic column, and the product was eluted with 8 l of ca. 8N ammonium hydroxide. The eluate was concentrated with heating until a thick precipitate formed. The mixture was cooled and filtered to yield 44 g (42%). The filtrate was evaporated to dryness, and the residue was triturated with 50 ml of hot water on a steam bath. The suspension was filtered, the filtrate was chilled at 5° for 3 days, and the solid was collected to give an additional 11 g. The combined yield was 52% of chromatographically homogeneous product, mp 254°–262° dec; $R_f$ 0.7 on silica gel in $CHCl_3$-MeOH (9:1). A sample for analysis was twice recrystallized from $H_2O$, mp 261°–264° dec.

H. 6-(4-Amino-4,6-dideoxy-β-L-glucopyranosylamino)-9H-purine). A solution of 4.1 g (0.013 mol) of the azide of paragraph G in 40 ml of MeOH-$H_2O$ (1:1) was treated with 0.40 g of 10% Pd/C and shaken under $H_2$ at 2–3 atm for 3 days. The catalyst was collected on a filter, washed with 25 ml of $H_2O$, and the combined filtrate was evaporated to dryness. A solution of the residue (4.0 g) in 50 ml of hot MeOH was clarified by filtration and cooled. The resultant precipitate was collected to yield 1.66 g (44%) of amorphous solid, free of IR bands for $N_3$. The filtrate was poured into 500 ml of ethyl ether to precipitate an additional 2.3 g (total yield 61%) that was identical by IR and TLC, $R_f$ 0.5 on silica gel (UV absorbing and ninhydrin positive spot) with contaminants of $R_f$ 0.1 and 0.9 (UV absorbing only) in $CHCl_3$-MeOH (1:1). This compound has the structure:

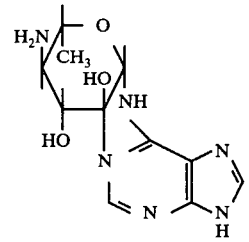

The following paragraphs I – L describe the preparation of various intermediates leading to the formation of the fatty acid- amino acid amoiety which is then reacted with the sugar adenine moiety of paragraph H so as to form the desired septacidin analog of the present invention.

I. (Z)-14-Methyl-11-pentadecenoic acid. 10-(Methoxycarbonyl)-decyltriphenylphosphonium iodide having a melting point of 126°–129° (N. Petragnani and G. Schill, Chem. Ber., 97, 3293, (1964)), was treated with NaOMe and $HCONMe_2$ to give $Ph_3PCH(CH_2)_9$—COOMe. It was then treated with isovaleraldehyde (($CH_3)_2CHCH_2CH=O$)(as with valeraldehyde in the Pentragnani et al. process) to give methyl (Z)-14-methyl-11-pentadecenate (83% yield) as a yellow oil; PMR ($CDCl_3$) δ 5.44 m (CH=CH), 3.70s ($COOCH_3$), 0.90d ($Me_2C$, J = 6.0 Hz). The ester, without distillation, still contained 5% triphenylphosphine oxide. Saponification afforded 78% of (Z)-14-methyl-11-pentadecenoic acid, free of $Ph_3PO$. A sample was distilled, bp 134°–136° (0.003 mm), mp 12.5°.

J. 14-Methylpentadecanoic acid (isopalmitic acid). Hydrogenation of the olefinic acid of paragraph I by shaking a 95% EtOH solution (4 ml/g) with 5% Pd/C under 3 atm of $H_2$, filtration, evaporation of the filtrate, and EtOH recrystallization of the residue gave the acid (53% yield), mp 62°–63°.

K. Isopalmitoylglycine. By the method of M. Fieser, L. Fieser, E. Toromanoff, Y. Hirata, H. Heymann, M.

Tefft and S. Bhattacharya, *J. Amer. Chem. Soc.*, 78, 2825 (1956), for stearoyl-β-alanine, the acid of paragraph J and glycine yielded 48%, recrystallized from EtOAc, mp 101°–103°.

L. p-Nitrophenyl isopalmitoylglycinate. A mixture of 1.67 g (5.29 mmol) of the acid of paragraph K and 0.75 g (5.4 mmol) of p-nitrophenol in 50 ml of EtOAc was stirred and cooled to 0°. The solution was treated with 1.10 g (5.34 mmol) of dicyclohexylcarbodiimide. The suspension was stirred at 0° for 30 min, at room temperature for 30 min, heated to 35°–40° for 3 hr, and cooled to 5°. Four drops of HOAc were added, the mixture was filtered, and the filtrate was evaporated. The residue was dissolved in 50 ml of ethyl ether with heating, the solution was clarified of any dicyclohexylurea by filtration, was diluted to the cloud point with pet. ether (bp 60°–110°), and was chilled overnight at −10°. The white solid was collected by filtration to yield 2.08 g (90%), mp 87°–89°. This compound has the structure:

M. The final reaction: 6-[4,6-Dideoxy-4-(isopalmitoylglycyl)amino-β-L-glucopyranosylamino]-9H-purine. A mixture of 8.41 g (30.0 mmol) of the compound of paragraph H and 13.2 g (30.4 mmol) of the compound of paragraph L in 300 ml of anhydrous dimethylformamide was stirred at 35° for 24 hr, and the solution was poured into 3 l of cold water. Stirring was continued for 1 hr, and the yellow precipitate was collected by filtration, washed with 1 l of water, and dried to yield 15.1 g (88%). Refluxing with 500 ml of MeOH and 5 ml of (Me₂CH)₂NH to cleave any ester bonds, followed by six recrystallizations (100 ml/g) alternately from absolute MeOH, MeOH-CHCl₃, and finally MeOH-H₂O gave 8.8 g (50%), mp 229°–232° dec; purity 99.65% by HPLC. Anal. (C₂₉H₄₉N₇O₅·0.5H₂O). This compound has the structure:

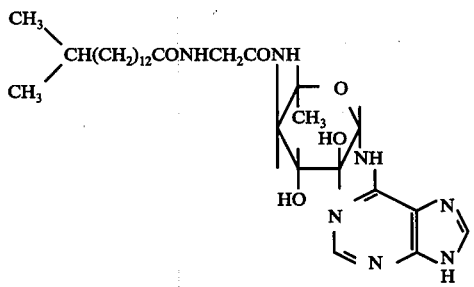

It is a white powder, moderately soluble in CH₃OH and slightly soluble in H₂O or saline.

EXAMPLE II

6-[4,6-Dideoxy-4-(lauroylglycyl)amino-β-L-glucopyranosylamino]-9H-purine

A mixture of 1.54 g (4.08 mmol) of p-nitrophenyl lauroylglycinate (A. Aszalos, P. Lemanski, and B. Berk, *J. Chem. Eng. Data*, 11, 429 (1966)), mp 98°–99.5°, and 1.10 g (3.92 mmol) of the compound of paragraph H of Example I in 25 ml of dry dimethylformamide was stirred at 35° for 18 hr, and the solution was poured into 500 ml of ice and water. Stirring was continued for 1 hr and the precipitate was stirred and washed with 100 ml of H₂O. A solution of solid in 50 ml of MeOH and 1 ml of diisopropylamine was refluxed for 1 hr to cleave selectively any ester bonds, and was evaporated. The solid (1.9 g, 90%) was triturated with hot ethyl acetate, the suspension was cooled, and the solid was collected on a filter. It was recrystallized from 40 ml with hot MeOH by adding 5 ml of H₂O and chilling to −10° to give 1.5 g. Another recrystallization from 15 ml of hot MeOH gave 0.63 g (30%), mp 219°–223° dec. that was chromatographically homogeneous on silica gel, R_f 0.50 in CHCl₃-MeOH (3:1). Anal. (C₂₅H₄₁—N₇O₅·0.5H₂O), C. H. N. This compound has the structure:

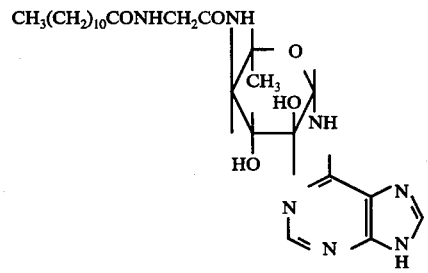

It is a white powder, moderately soluble in CH₃OH and slightly soluble in H₂O or saline.

EXAMPLE III

6-[4,6-Dideoxy-4-(myristoylglycyl)amino-β-L-glucopyranosylamino]-9H-purine

This compound is prepared by the general method of Example II except that p-nitrophenyl myristoylglycinate is employed instead of p-nitrophenyl lauroylglycinate.

EXAMPLE IV

6-[4,6-Dideoxy-4-(tridecanoylglycyl)amino-β-L-glucopyranosylamino]-9H-purine

This compound is prepared by the general method of Example II except that p-nitrophenyl tridecanoylglycinate is employed instead of p-nitrophenyl lauroylglycinate.

EXAMPLE V

6-[4,6-Dideoxy-4-(palmitoylglycyl)amino-β-L-glucopyranosylamino]-9H-purine

This compound is prepared by the general method of Example II except that p-nitrophenyl palmitoylglycinate is employed instead of p-nitrophenyl lauroylglycinate.

EXAMPLE VI

6-[4,6-Didoexy-4-(caproylglycyl)amino-β-L-glucopyranosylamino]-9H-purine

This compound is employed herein for comparative purposes only. On being prepared, it was found that this compound (where R of the general formula given above has a value of 6) was inactive for antitumor applications.

BIOLOGICAL TESTS

Biological testing data for compounds of this invention, as well as for septacidin and adriamycin, are presented in the table given below.

The septacidin analogs 2 and 3 (corresponding to the compounds of Examples I and II, respectively) were tested first in cultured lymphoid leukemia L1210 cells for inhibition of nucleic acid syntheses and for cytotoxicity, by previously reported procedures. A sample of natural septacidin (compound 1) was obtained from the National Cancer Institute and included for comparison. Data on adriamycin (compound 4) are also included. The analogs were then tested, along with 1 and 4, against lymphocytic leukemia P388 implanted in mice, under the auspices of the NCI and according to its protocols which use the increased survival time of treated animals compared to controls as the measure of antitumor efficacy. The mouse tests clearly show that synthetic analogs 2 and 3 retain the high antitumor potency of 1, with "confirmed activity" according to NCI criteria, at doses of 0.5–1.0 mg/kg. In vitro, analog 2 showed a response nearly the same as 1 in the RNA test but not as potent as the DNA test. Analog 3 was noticeably less potent.

When the fatty acid was shortened from 16 carbons (2) to 12 carbons (3) there was decreased activity in vitro and a slight loss of efficacy in vivo. When shortened to 6 carbons (Example VI), loss of activity was total. Thus, lipophilic character is important.

The data suggest that chain branching is not required, and that palmitic acid can be substituted in synthetic structures for the difficultly accessible isopalmitic acid. (Example V).

Comparison of both in vivo and in vitro data shows that 2 is comparable in potency to the highly important anthracycline antibiotic for the treatment of cancer, adriamycin. The in vivo efficacy of adriamycin is much higher, but there are other differences. Adriamycin is highly cytotoxic, while cytotoxic effects of 2 could not be observed at soluble levels. Adriamycin binds strongly to isolated helical DNA in solution (as measured by its effect on the helix-coil transition temperature of the DNA, or $\Delta T_m$) whereas 2 binds only weakly. This suggests that the potent inhibition of nucleic acid synthesis by 2 may be an indirect effect.

BIOLOGICAL TEST RESULTS

| Compound No. | NSC[a] No. | Vs Cultured L1210 Leukemia Cells[b] | | | Vs P388 Leukemia in Mice[c] | | Binding to Isolated Helical DNA in Solution[b] $\Delta T_m$, °C |
| --- | --- | --- | --- | --- | --- | --- | --- |
| | | Inhibition of Synthesis | | Cytotoxicity $I_{50}$, μM | Optimum Dose, qd 1-9 mg/kg | Antitumor Efficacy T/C, % | |
| | | of DNA $Ed_{50}$, μM | of RNA $ED_{50}$, μM | | | | |
| 1 Septacidin[d] | 65104 | 0.30 (0.23) | 0.70 (0.53) | >5 | 0.50 (0.38) | 154 | — |
| 2 | 268251 | 2.6 | 0.88 | >20 | 1.0 | 160 | 0.6 |
| 3 | 266218 | 29 | 18 | >10 | 1.0 | 137 | — |
| 4 Adriamycin[e] | 123127 | 1.5 | 0.67 | 0.032 | 1.0 | 193 | 13.6 |

[a]Accession number of the National Cancer Institute.
[b]Assay described in G. Tong, W. W. Lee, D. R. Black and D. W. Henry, J. Med. Chem., 19, 395 (1976).
[c]Assay described in R. I. Geran, N. H. Greenberg, M. M. MacDonald, A. M. Schumacker and B. J. Abbott, Cancer Chemother. Rep., Part 3, 3 (No. 2), 9 (1972). Protocol 1.200. Other doses were higher or lower by a factor of 2. Each compound has 2–4 active doses. Compounds were of borderline solubility, and some doses were injection as suspensions. Water, water + Tween 80, or saline + Tween 80 (emul. agent, ICI) were used as vehicles. By definition, a compound is active if T/C ≦ 125. For compounds 2 and 3 the T/C is the average from two tests. Optimum dose is the one producing the highest T/C.
[d]Purity of 1 was estimated to be 75%, based on elemental analysis for N; corrected doses, assuming inactive impurities, are shown in parentheses.
[e]Data from G. Tong, W. W. Lee, D. R. Black and D. W. Henry, J. Med. Chem., 19, 395 (1976). The $\Delta T_m$ of the 13.6° was obtained by the modified procedure.

What is claimed is:
1. A compound having the structure

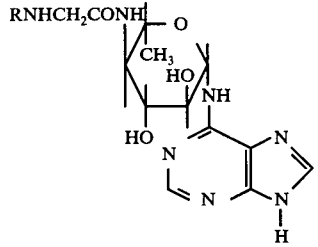

where R is an alkanoyl radical of from 12 to 16 carbon atoms.

2. The compound of claim 1 which is 6-[4,6-dideoxy-4-(isopalmitoylglycyl)amino-β-L-glucopyranosylamino]-9H-purine.

3. The compound of claim 1 which is 6-[4,6-dideoxy-4-(lauroylglycyl)amino-β-L-glucopyranosylamino]-9H-purine.

* * * * *